US006605310B2

(12) United States Patent
Fuchs et al.

(10) Patent No.: US 6,605,310 B2
(45) Date of Patent: Aug. 12, 2003

(54) CALORICALLY DENSE LIQUID ORAL SUPPLEMENT

(75) Inventors: Eileen Fuchs, Gaylordsville, CT (US); Chandrasekhara R. Mallangi, New Milford, CT (US); Peter Carhuff, Gaylordsville, CT (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/681,795

(22) Filed: Jun. 6, 2001

(65) Prior Publication Data

US 2002/0192354 A1 Dec. 19, 2002

(51) Int. Cl.[7] .............................. A23L 1/29; A23J 1/14; A23J 1/20
(52) U.S. Cl. ...................... 426/656; 426/634; 426/580; 426/800; 426/801; 426/810; 426/648; 514/2
(58) Field of Search ................................ 426/656, 634, 426/580, 648, 800, 801, 810; 514/2

(56) References Cited

U.S. PATENT DOCUMENTS

| | | |
|---|---|---|
| 4,112,123 A | 9/1978 | Roberts |
| 4,358,465 A | 11/1982 | Brule et al. |
| 4,361,587 A | 11/1982 | Brule et al. |
| 4,427,658 A | 1/1984 | Maubois et al. |
| 4,495,176 A | 1/1985 | Brule et al. |
| 4,670,268 A | 6/1987 | Mahmoud |
| 4,740,462 A | 4/1988 | Brule et al. |
| 4,753,963 A | 6/1988 | Jandacek et al. |
| 4,816,398 A | 3/1989 | Brule et al. |
| 4,920,098 A | 4/1990 | Cotter et al. |
| 4,931,300 A | 6/1990 | Monte |
| 4,980,450 A | 12/1990 | Brule et al. |
| 5,028,589 A | 7/1991 | Brule et al. |
| 5,053,387 A | 10/1991 | Alexander |
| 5,055,446 A | 10/1991 | Alexander et al. |
| 5,108,767 A | 4/1992 | Mulchandani et al. |
| 5,156,875 A | 10/1992 | Monte |
| 5,166,189 A | 11/1992 | Trimbo et al. |
| 5,221,668 A | 6/1993 | Henningfield et al. |
| 5,223,285 A | 6/1993 | DeMichele et al. |
| 5,260,279 A | 11/1993 | Greenberg |
| 5,308,832 A | 5/1994 | Garleb et al. |
| 5,340,603 A | 8/1994 | Neylan et al. |
| 5,422,127 A | 6/1995 | Dube et al. |
| 5,438,042 A | 8/1995 | Schmidl et al. |
| 5,470,839 A | * 11/1995 | Laughlin et al. |
| 5,480,872 A | 1/1996 | Cope et al. |
| 5,504,072 A | 4/1996 | Schmidl et al. |
| 5,547,927 A | 8/1996 | Cope et al. |
| 5,549,905 A | 8/1996 | Mark et al. |
| 5,550,106 A | * 8/1996 | Petschow et al. |
| 5,574,065 A | 11/1996 | Trimbo |
| 5,589,468 A | 12/1996 | Lin et al. |
| 5,635,199 A | 6/1997 | Trimbo |
| 5,661,123 A | 8/1997 | Stalker et al. |
| 5,700,782 A | 12/1997 | Cope et al. |
| 5,700,837 A | 12/1997 | Trimbo |
| 5,714,472 A | 2/1998 | Gray et al. |
| 5,723,446 A | 3/1998 | Gray et al. |
| 5,733,884 A | 3/1998 | Barbul et al. |
| 5,766,621 A | 6/1998 | Trimbo et al. |
| 6,322,835 B1 | * 11/2001 | De Soete et al. |
| 6,376,544 B2 | * 4/2002 | Lowry et al. |

FOREIGN PATENT DOCUMENTS

| | | |
|---|---|---|
| EP | 0 189 160 | 7/1986 |
| EP | 0 721 742 A1 | 7/1996 |
| WO | 97/16079 | 9/1997 |

OTHER PUBLICATIONS

Alexander et al., "Beneficial Effects of Aggressive Protein Feeding in Severely Burned Children", *Ann. Surg.*, vol. 192, No. 4, 1980, pp. 505–517.

Anderson et al., "Intestinal Protein Loss During Enteral Alimentation in Critically Ill Patients", *J Parenter Enteral Nutr.*, vol. 14 (Suppl), No. 1, 1990, p. 24, Abstract.

August et al., "Determination of Zinc and Copper Absorption at Three Dietary Zn—Cu Ratios by Using Stable Isotope Methods in Young Adult and Elderly Subjects", *Am J Clin Nutr*, vol. 50, 1989, pp. 1457–1463.

Austin, "Water: Guidelines for Nutritional Support", *Nutritional Support Services*, vol. 6, No. 9, 1986, pp. 27–29.

Belcher et al., "Determinants of Urinary Nitrogen Excretion in Burned Patients", *Burns*, vol. 14, No. 4, 1988, pp. 303–307.

Bell et al., "Alternative lipid sources for enteral and parenteral nutrition: Long– and medium–chain triglycerides, structured triglycerides, and fish oils", *Journal of the American Dietetic Association*, vol. 91, No. 1, 1991, pp. 74–78.

Bjerve et al., "Alpha–Linolenic Acid Deficiency in Patients on Long–Term Gastric–Tube Feeding: Estimation of Linolenic Acid and Long–Chain Unsaturated n–3 Fatty Acid Requirement in Man", *Am J Clin Nutr*, vol. 5, 1987, pp. 66–77.

Bjerve et al., "Alpha–linolenic acid deficiency in man: effect of ethyl linolenate on plasma and erythrocyte fatty acid composition and biosynthesis of prostanoids", *Am J Clin Nutr*, vol. 46, 1987, pp. 570–576.

Bogden et al., "Zinc and Immunocompetence in Elderly People: Effects of Zinc Supplementation for 3 Months", *Am J Clin Nutr*, vol. 48, 1988, pp. 655–663.

Bogden et al., "Zinc and Immunocompetence in the Elderly: Baseline Data on Zinc Nutriture and Immunity in Unsupplemented Subjects", *Am J Clin Nutr*, vol. 46, 1987, pp. 101–109.

(List continued on next page.)

*Primary Examiner*—Anthony J. Weier
(74) *Attorney, Agent, or Firm*—Bell, Boyd & Lloyd LLC

(57) ABSTRACT

The present invention provides a liquid oral supplement and a method for using the same. The supplement provides at least 2.25 calories per ml and provides at least 15% by caloric content of protein.

13 Claims, No Drawings

OTHER PUBLICATIONS

Borum, "Role of Carnitine in Lipid Metabolism", *Lipids in Modern Nutrition,* New York: Raven Press, 1987, pp. 51–58.

Borum et al., "Carnitine content of liquid formulas and special diets", *Am J Clin Nutr,* vol. 32, 1979, pp. 2272–2276.

Breslow, "Nutritional Status and Dietary Intake of Patients With Pressure Ulcers: Review of Research Literature 1943 to 1989", *Decubitus,* vol. 4, No. 1, 1991, pp. 16–21.

Brinson, "The Effect of Peptide–Based Diets on the Intestinal Microcirculation in a Rat Model", *Nutr Clin Prac,* vol. 5, 1990, pp. 238–240.

Brinson et al., "Diarrhea Associated with Severe Hypoalbuminemia: A Comparison of a Peptide–Based Chemically Defined Diet and Standard Enteral Alimentation", *Critical Care Medicine,* vol. 16, No. 2, 1988, pp. 130–136.

Brinson et al., "Intestinal Absorption of Peptide Enteral Formulas in Hypoproteinemic (Volume Expanded) Rats: A Paired Analysis", *Critical Care Medicine,* vol. 17, No. 7, 1989, pp. 657–660.

Bynoe et al., "Nutrition Support in Trauma Patients", *Nutr. Clin. Prac,* vol. 4, 1988, pp. 137–144.

Cerra et al., "Enteral Nutrition in Hypermetabolic Surgical Patients", *Critical Care Medicine,* vol. 17, No. 7, 1989, pp. 619–622.

Cerra et al., "The Effect of Stress Level, Amino Acid Formula, and Nitrogen Dose on Nitrogen Retention in Traumatic and Septic Stress", *Ann. Surg.,* vol. 205, No. 3, 1987, pp. 282–287.

Cerra et al., "What's New in Nutrition Support in Critical Care", *Perspective in Clinical Nutrition,* Kinney, Borum (Eds.), Urban & Schwarzenberg: Baltimore–Munich, 1989, pp. 323–338.

Chandra, "Trace Element Regulation of Immunity and Infection", *Journal of the American College of Nutrition,* vol. 4, No. 1, 1985, pp. 5–16.

Chernoff et al., "The effect of a very high–protein liquid formula (Replete®) on decubitus ulcer healing in long–term tube–fed institutional patients", *J Am Diet Assoc.,* vol. 90, 1991.

Clintec Nutrition Company, Proper Nutrition For ICU Patients Is Critical, Brochure, 1994.

Clintec Nutrition Company, When You Create Such A Unique Enteral Formula, It's Hard Not To Create Attention, Brochure, 1994.

Clintec Nutrition Company, Crucial Needs Require A Crucial™ Solution, Brochure, 1994.

Clintec Nutrition Company, Crucial™ Compared To Perative®, Brochure, 1995.

Clintec Nutrition Company, When Your First Choice Has To Be Your Best Choice, Reabilan™ Brochure (Undated).

Clintec Nutrition Company, Reabilan HN, Brochure (Undated).

D'Atellis et al., "Branched–Chain Amino Acids", *Nutrition in Critical Care,* In Zaloga (ed.), St. Louis, MO: Mosby, 1994, pp. 81–106.

Dominioni et al., "Enteral Feeding in Burn Hypermetabolism: Nutritional and Metabolic Effects of Different Levels of Calorie and Protein Intake", *Journal of Parenteral and Enteral Nutrition,* vol. 9, No. 3, 1985, pp. 269–279.

Dominioni et al., "Prevention of Severe Postburn Hypermetabolism and Catabolism by immediate Intragastric Feeding", *J. Burn Care Rehab.,* vol. 5, No. 2, 1984, pp. 106–112.

Ehrlich et al., "Effects of Cortisone and Vitamin A on Wound Healing", *Annals of Surgery,* vol. 167, No. 3, 1968, pp. 324–328.

Ehrlich et al., "Effects of Vitamin A and Glucocorticoids upon Inflammation and Collagen Synthesis", *Ann. Surg.,* vol. 177, No. 2, 1973, pp. 222–227.

Ehrlich et al., "Effects of Beta–Carotene, Vitamin A, and Glucocorticoids on Collagen Synthesis in Wounds", *Proc. Soc. Exp Biol Med.,* vol. 137, No. 1, 1971, pp. 936–938.

Fabiani et al., "Oral Hyperalimentation in the Nutritional Management of Burned Patients", *SAMJ,* vol. 67, 1985, pp. 768–770.

Freeman et al., "Effects of Magnesium Infusions on Magnesium and Nitrogen Balance During Parenteral Nutrition", *The Canadian Journal of Surgery,* vol. 25, No. 5, 1982, pp. 570–574.

Geggel et al., "Nutritional Requirement for Taurine in Patients Receiving Long–Term Parenteral Nutrition", *The New England Journal of Medicine,* vol. 312, No. 3, 1985, pp. 142–146.

Goodson et al., "Wound Healing", *Nutrition and Metabolism in Patient Care,* In: Kinney et al. (Eds.), Philadelphia, PA: WB Saunders, 1988, 635–642.

Gottschlich et al., "Enteral Nutrition in Patients with Burns or Trauma", *Clinical Nutrition Enteral and Tube Feeding 2nd Edition,* In: Rombeau et al. (Eds.), Philadelphia, PA: WB Saunders, 1990, pp. 306–324.

Gottschlich et al., "Vitamin Supplementation in the Patient with Burns", *J. Burn Care Rehab.,* vol. 11, No. 3, 1990, pp. 275–279.

Granger et al., "Intestinal Absorption of Elemental and Standard Enteral Formulas in Hypoproteinemic (Volume Expanded) Rats", *Journal of Parenteral and Enteral Nutrition,* vol. 12, No. 3, 1988, pp. 278–281.

Greenberger et al., "Medium–Chain Triglycerides: Physiologic Considerations and Clinical Implications", *The New England Journal of Medicine,* vol. 280, No. 19, 1969, pp. 1045–1058.

Hadley et al., "Nutrition and Wound Healing", *Top Clin. Nutr.,* vol. 5, No. 4, 1990, pp. 72–81.

Hallbook et al, "Serum–Zinc and Healing of Venous Leg Ulcers", *Lancet,* 1972, pp. 780–782.

Hayes, "Vitamin–Like Molecules (D) Taurine", *Modern Nutrition in Health and Disease,* 7th Edition, Philadelphia: Lea and Febiger, 1988, pp. 464–470.

Heymsfield et al., "Respiratory, cardiovascular, and metabolic effects of enteral hyperalimentation: influence of formula dose and composition", *The American Journal of Clinical Nutrition,* vol. 40, 1984, pp. 116–130.

Holman, "Function and Biologic Activities of Essential Fatty Acids in Man", *Fat Emulsion in Parenteral Nutrition,* Chicago: American Medical Association, 1976, pp. 5–14.

Holt, "Medium Chain Triglycerides: A Useful Adjunct in Nutritional Therapy", *Gastroenterology,* vol. 53, No. 6, 1967, pp. 961–966.

Hunt, "Control of Wound Healing With Cortisone and Vitamin A", *The Ultrastructre of Collagen,* In: Longacre JJ (ed.), Springfield, IL: Charles C. Thomas, 1976, pp. 497–508.

Hunt et al., "Effect of Vitamin A on Reversing the Inhibitory Effect of Cortisone on Healing of Open Wounds in Animals and Man", *Annals of Surgery,* vol. 170, No. 4, 1969, pp. 633–641.

Hunt et al., "Selenium Depletion in Burn Patients", *Journal of Parenteral and Enteral Nutrition*, vol. 8, No. 6, 1984, pp. 695–699.

Ireton–Jones et al., "Nutrition for Adult Burn Patients: A Review", *Nutr. Clin Prac.*, vol. 6, No. 1, 1991, pp. 3–7.

Jahoor et al., "Dynamics of the Protein Metabolic Response to Burn Injury", *Metabolism*, vol. 37, No. 4, 1988, pp. 330–337.

Johnson et al., "Metabolism of Medium–Chain Triglyceride Lipid Emulsion", *Nutrition International*, vol. 2, No. 3, 1986, pp. 150–158.

Joint FAO/WHO Ad Hoc Expert Committee, "Protein and Energy Requirements: a joint FAO/WHO Memorandum," *Bulletin of the World Health Organization*, vol. 57, 1979, pp. 65–79.

Kaunitz, "Clinical uses of medium–chain triglycerides", *Drug Therapy*, vol. 8, 1978, pp. 91–96.

Kissileff et al., "Physiology of the Control of Food Intake", *Ann. Rev. Nutr.*, vol. 2, 1982, pp. 371–418.

Kubo et al., "Fluid and Electrolyte Problems of Tube–Fed Patients", *American Journal of Nursing*, vol. 76, No. 6, 1976, pp. 912–916.

Law et al., "The Effect of Dietary Protein Depletion in Immunocompetence: The Importance of Nutritional Repletion Prior to Immunologic Induction", *Ann. Surg.*, vol. 179, No. 2, 1974, pp. 168–173.

Levenson, "Micronutrients (Vitamins, Trace Minerals)", In ASPEN Program Manuel of Proceedings of The 16th Clinical Congress, 1992, pp. 189–198.

Long et al., "Metabolic Response to Injury and Illness: Estimation of Energy and Protein Needs from Indirect Calorimetry and Nitrogen Balance", *Journal of Parenteral and Enteral Nutrition*, vol. 3, No. 6, 1979, pp. 452–456.

Mahan et al., "The Assessment of Nutritional Status", *Krause's Food Nutrition & Diet Therapy*, 8th Edition, Philadelphia: W.B. Saunders Company, 1992, pp. 293–313.

Mandt et al., "Nutritional Requirements", *Nutrition Support Handbook*, In: Teasley–Strausberg (ed.), Cincinnati, OH: Harvey Whitney Books Co., 1992, pp. 19–36.

Mascioli et al., "Intravenous Infusion of a Physical Mixture of Medium and Long Chain Triglyceride Emulsion", *Clin. Res.*, vol. 33, 1985, 275A.

McClave et al., "Immunonutrition and Enteral Hyperalimentation of Critically Ill Patients", *Digestive Diseases and Sciences*, vol. 37, No. 8, 1992, pp. 1153–1161.

Mead Johnson, *Enteral Nutritionals Product Handbook*, bearing Nos. A2688–2693.

Mead Johnson Enteral Nutritionals Brochure bearing Nos. B00083.

Mead Johnson Brochure bearing Nos. B00322–B00323.

Mead Johnson, *Metabolic and Nutrition Support for Trauma and Burn Patients A Symposium*, Abstracts, 1982, pp. 1–13.

Meredith et al., "Visceral Protein Levels in Trauma Patients Are Greater with Peptide Diet Than with Intact Protein Diet", *The Journal of Trauma*, vol. 30, No. 7, 1990, pp. 825–829.

National Research Council, "Recommended Dietary Allowances, 10th Edition," Washington, D.C.: National Academy Press 1989.

Nichols et al., "Magnesium supplementation in protein–calorie malnutrition", *The American Journal of Clinical Nutrition*, vol. 31, 1978, pp. 176–188.

*Nutritional Care of Metabolically Stressed Patients*, Proceedings from the Metabolic and Nutrition Support for Trauma and Burn Patients Symposium, White Sulphur Springs, West Virginia, 1983, pp. 1–77.

Ortiz et al., A Comparative Post–Operative Study—An Enteral Solution Based on Free Amino Acids, *Gastroenterologic Clinique et Biologique*, vol. 9, No. 2, 1985, pp. 182–183.

Pearson et al., "An Estimation of the Potassium Requirements For Equilibrium in Burned Patients", *Surgery Gynecology & Obstetrics*, vol. 112, No. 3, 1961, pp. 263–273.

Pories et al., "Acceleration of Wound Healing in Man With Zinc Sulphate Given By Mouth", *Lancet*, 1967, pp121–124.

Prasad et al., "Serum Thymulin in Human Zinc Deficiency", *J. Clin. Invest.*, vol. 82, 1988, pp. 1202–1210.

*Principles of Nutritional Support: Proceedings From the Metabolic and Nutrition Support for Trauma and Burn Patients Symposium*, White Sulphur Springs, West Virginia, 1982, pp. 1–25.

Randall et al., "Randomized Clinical Trial in Hospitalized Patients Using Intravenous Medium Chin Trigylceride Emulsions", *Clin. Res.*, vol. 33, 1985, 276A.

Ringsdorf et al., "Vitamin C and Human Wound Healing", *Oral Surgery*, vol. 53, No. 3, 1982, pp. 231–236.

Ross et al., "Wound Healing and Collagen Formation—II. Fine Structure in Experimental Scurvy", *The Journal of Cell Biology*, vol. 12, 1962, pp. 533–551.

Ross et al., "Wound Healing and Collagen Formation—V. Quantitative Electron Microscope Radioautographic Observations of Proline–$H^3$ Utilization by Fibroblasts", *The Journal of Cell Biology*, vol. 27, 1965, pp. 83–106.

Ross et al., "Vitamin A as a Hormone: Recent Advances in Understanding the Actions of Retinol, Retinoic Acid, and Beta Carotene", *Journal of The American Dietetic Association*, vol. 93, No. 11, 1993, pp. 1285–1290.

Ross Laboratories Brochure, Specialized Elemental Nutrition With Glutamine—The Role of ALITRAQ™ Specialized Elemental Nutrition With Gluamine, 1991.

Ross Laboratories Brochure, Introducing ALITRAQ™ Specialized Elemental Nutrition With Glutamine, 1992.

Ross Laboratories Brochure, Introducing PERATIVE™, 1992.

Sailer et al., "Medium Chain Triglycerides in Parenteral Nutrition" *Journal of Parenteral and Enteral Nutrition*, vol. 5, No. 2, 1981, pp. 115–119.

Sandoz Nutrition Brochure, IMPACT®, 1993.

Sandoz Nutrition Brochure, Introducing IMPACT®, 1989.

Sandoz Nutrition Brochure, IMPACT®, 1991.

Sandstead et al., "Zinc and Wound Healing: Effects of Zinc Deficiency and Zinc Supplementation", *The American Journal of Clinical Nutrition*, vol. 23, No. 5, 1970, pp. 514–519.

Silk, "Nutritional Support in Hospital Practice", Oxford, Blackwell Scientific Publications, 1983, pp. 79–82.

Simopoulos, "Omega–3 fatty acids in health and disease and in growth and development", *Am J Clin Nutr*, vol. 54, 1991, pp. 438–463.

Spiller et al., "Malabsorption", *Nutrition and Metabolism in Patient Care*, Kinney et al. (Eds.), Philadelphia, PA: WB Saunders, 1988, pp. 281–304.

Stotts et al., "Nutrition: A Critical Component of Wound Healing", *AACN Clin Issues*, vol. 1, No. 3, 1990, pp. 585–594.

Sturman et al., "The Biology of Taurine in Nutrition and Development", *Adv. Nutr Res.* vol. 3, 1980, pp. 231–299.

Sucher, "Medium Chain Triglycerides: A Review of Their Enteral Use in Clinical Nutrition", *Nutrition in Clinical Practice,* 1986, pp. 146–150.

*Symposium Highlights Metabolic and Nutrition Support for Trauma and Burn Patients,* White Sulphur Springs, West Virginia, 1982, pp. 1–26.

Szebeni et al., "Vitamin A Levels in the Serum of Burned Patients", *Burns,* vol. 7, No. 5, 1981, pp. 313–318.

TraumaCal, *Feeding the Hypermetabolic Patient, Clinical Experience, A Symposium,* 1983, pp. 1–74.

TraumaCal Product Cards bearing Nos. B000001–10.

TraumaCal Documents bearing Nos. B00088–105.

TraumaCal Document bearing Nos. B00181.

TraumaCal Document bearing Nos. B00261–265.

TraumaCal Document bearing No. B00293.

TraumaCal Document bearing Nos. B00384–385.

TraumaCal Label bearing No. B00441.

TraumaCal Brochure bearing Nos. B00567–570.

Twyman et al., "High Protein Enteral Feedings: A Means of Achieving Positive Nitrogen Balance in Head Injured Patients", *Journal of Parental and Enteral Nutrition,* vol. 9, No. 6, 1985, pp. 679–684.

Waxman et al., "Protein Loss Across Burn Wounds", *The Journal of Trauma,* vol. 27, No. 2, 1987, pp. 136–140.

Ziegler et al., "Efficiency of Enteral Nitrogen Support in Surgical Patients: Small Peptides v Non–Degraded Proteins", *Gut,* vol. 31, 1990, pp. 1277–1283.

\* cited by examiner

CALORICALLY DENSE LIQUID ORAL SUPPLEMENT

BACKGROUND OF THE INVENTION

The present invention generally relates to a composition for providing nutrition. More specifically, the present invention relates to liquid oral supplements having increased caloric and protein content.

The human body requires energy to perform its vital functions, such as blood circulation, immune processes, respiration processes, etc. Energy can be supplied in the form of calories. Calories are typically supplied by the consumption of food. Calorie sources can be classified into three categories: proteins, fats, and carbohydrates. Proteins can provide the body with support for muscular activity; fats can provide the body with stored energy; and carbohydrates can supply the body with immediate energy. Essential vitamins and minerals are necessary to help regulate the processes of the human body.

An individual needs to receive a proper balance of nutrients to sustain health; otherwise, malnutrition can result in a variety of physical complications. Moreover, it is imperative that the support provided be adapted to the needs of an individual. For example, patients who are ill require increased and specialized nutritional support. An increase in specific nutrients can help the body recover from a particular stress placed upon it.

Nutritional needs can also change with a person's age. For example, elderly individuals show a decrease in the amount of energy their body requires from fat sources. This is attributed to a decrease in the number of functioning cells an elderly individual has. This is also attributed to a decrease in activity. Accordingly, an elderly individual's nutritional requirements may be different than a young or middle aged individual.

Because at least certain individuals may not receive their required nutritional support from a normal diet, nutritional supplements have been designed to provide nutritional support to individuals. The supplements can be directed towards a particular type of nutritional support. For example, a supplement may provide an individual with additional calories for increased energy. Although these supplements provide a certain amount of nutritional support, it is in the best interests to provide a composition having increased nutritional value for a specific nutritional requirement.

In the above examples of elderly individuals and ill patients, it is desired to provide nutritional supplements having increased energy as well as increased protein per serving. In this regard, although an elderly individual's energy needs may be reduced, their ability to consume products may also be diminished. For example, they may have difficulty consuming a product due to, e.g., swallowing difficulties. Further, certain disease states or conditions may require restrictions on the diet a patient consumes. For example, renal patients may have fluid restrictive diets.

However, increasing both calories and/or protein in a nutritional supplement can increase the overall viscosity of the supplement. This can make the supplement difficult to consume or administer, and can also diminish the taste of the supplement.

Therefore, a need exists for improved oral supplements, for example, with an increased amount of protein and calories per ml for an elderly individual or ill patient.

SUMMARY OF THE INVENTION

The present invention provides a calorically dense liquid oral supplement. In an embodiment, the supplement is designed to help to meet the nutritional needs of elderly individuals as well as patients with certain disease states. The supplement provides an increased amount of calories per ml while providing a sufficiently low viscosity to allow the supplement to be easily consumed orally or be administered by tube feeding or other like manner. In addition, the taste of the supplement is not diminished despite the increase in calories and protein.

To this end, in an embodiment of the present invention, a liquid nutritional product is provided that includes a protein source that provides at least 15% of the total caloric content of the product. The protein source includes caseinate and soy. The product has a caloric density of at least 2.25 calories per ml.

In an embodiment, the liquid nutritional product includes a prebiotic, such as fructooligosaccharides.

In an embodiment, the protein source comprises at least 90 grams per liter of product.

In an embodiment, the fat source comprises at least 50% of the caloric content.

In an embodiment, the product has a viscosity of 100 centipoises or less.

In another embodiment of the present invention, a liquid nutritional product is provided having a protein source that provides at least 16% of the total caloric content of the product and includes caseinate and soy protein isolate. In addition, the product includes a fat source that provides at least 40% of the caloric content, and a carbohydrate source that provides at least 25% of the caloric content. The product has a caloric density of at least 2.25 calories per ml.

In yet another embodiment of the invention, a method for providing nutritional support to a patient is provided comprising the steps of administering a nutritional supplement to an individual requiring same. The nutritional supplement comprises a protein source that provides at least 15% of the total caloric content of the product and includes caseinate and soy. The product has a caloric density of at least 2.25 calories per ml. The amount of product administered is in the range of approximately 25 to about 100 ml per serving.

In an embodiment, the individual is an elderly individual.

In an embodiment, the individual is recovering from a disease state.

In an embodiment, the individual is stressed.

It is, therefore, an advantage of the present invention to provide an improved liquid oral supplement.

Moreover, an advantage of the present invention is to provide a nutritional supplement for an elderly individual.

Furthermore, an advantage of the present invention is to provide a nutritional product for individuals suffering from a disease state or recovering from a disease state.

Another advantage of the present invention is to provide a liquid oral supplement which provides an increased amount of protein.

Still another advantage of the present invention is to provide a liquid oral supplement which may be easily consumed.

Yet another advantage of the present invention is to provide a liquid oral supplement that provides an increased amount of calories per ml.

Another advantage of the present invention is to provide a liquid oral supplement having a taste acceptable to an individual.

Still another advantage of the present invention is to provide a liquid oral supplement having a low viscosity despite having an increased amount of protein.

Additional features and advantages of the present invention are described in and will be apparent from the detailed description of the presently preferred embodiments.

DETAILED DESCRIPTION OF THE INVENTION

The present invention provides a liquid oral supplement and methods of providing nutritional support to individuals. The supplement has an increased amount of caloric content as well as an increased level of protein. The supplement is designed, in a preferred embodiment, to provide nutrition to elderly individuals that may be malnourished, stressed individuals, e.g., those that may have a disease state, as well as patients recovering from a disease. The product despite having an increased caloric content retains a low viscosity such that it may be easily consumed or administered. Further, the taste of the product remains acceptable despite a high protein level.

The product is designed to either supplement an individual's diet or provide complete nutritional support. The product includes a protein source, a fat source, a carbohydrate source, and a source of vitamins and minerals.

The protein source provides at least 15% of the total caloric content of the supplement. In an embodiment, the protein source provides at least 16% of the total caloric content. For example, in an embodiment, 90 grams per liter of protein are provided per serving of product. The high levels of protein are beneficial for patients who may not be physically capable of receiving a large volume of product, for example, fluid restricted patients. Such patients can be given a reduced level of fluid while still receiving a required amount of nutritional support per day.

The protein source can consist of 100% caseinate. Because caseinate may increase the viscosity of the supplement, a blend of caseinate and soy protein isolate may be desired. The isolate may be whole, nicked or hydrolyzed. In an embodiment, a caseinate and soy protein isolate blend is used having a ratio of approximately 75:25 to approximately 50:50 respectively. For example, in an embodiment, the protein source consists of a blend of caseinate and soy protein isolate in a ratio of 70:30 respectively. This embodiment has a viscosity which is lower than that in which the protein source is 100% caseinate. For example, the viscosity of the 70:30 blend is approximately 95 centipoises. In an embodiment of the present invention, the protein source consists of a blend of caseinate and soy protein isolate in a ratio of 60:40 respectively. This embodiment displays a viscosity of approximately 85 centipoises.

As noted above, the product includes a fat source. The fat source can consist of medium chain triglycerides (MCT) or long chain triglycerides (LCT). Moreover, the fat source may be any combination of the two types. MCTs are beneficial because they are easily absorbed and metabolized in a metabolically-stressed patient. Moreover, the use of MCTs will reduce the risk of nutrient malabsorption. LCTs, such as canola or corn oil are preferred because they can reduce immune suppression associated with certain types of fatty acids concentrated in the body.

In an embodiment of the present invention, the fat source provides at least 40% of the caloric content. In a preferred embodiment, the fat source provides approximately 50% of the total caloric content. The fat source in an embodiment consists of a blend of canola and corn oil.

As noted above, the product includes a carbohydrate source. The carbohydrate source may comprise a variety of components (e.g., sucrose, corn syrup). The carbohydrate source preferably provides at least 25% of the total caloric content. In the preferred embodiment, the carbohydrate source provides approximately 35% of the caloric content.

The supplement can contain a variety of vitamins and minerals. In a preferred embodiment, the supplement provides all necessary vitamins and minerals. For example, the supplement preferably provides 60 mg of zinc per liter which is beneficial for tissue repair in a healing patient. The supplement also provides 250 mg of Vitamin C per liter to aid patients with more severe healing requirements. In addition, the supplement provides 22.5 mg of iron per liter. Iron is essential in maintaining bodily fluids as well as circulatory system functions in an elderly patient. Overall, the supplement preferably includes at least 100% of the United States Recommended Daily Allowance (USRDA) of vitamins and minerals in a one liter portion.

The supplement may be fortified with a prebiotic such as, for example, fructooligosaccharides or inulin. In an embodiment, the supplement provides 24 grams of a prebiotic per liter of product.

As noted above, the product preferably has a high caloric density. Preferably, the product provides at least 2.25 calories per ml. Although the product has a high caloric density, it also has a sufficiently low viscosity to allow it to be consumed by elderly individuals that may have difficulty swallowing products or those that are tube fed. Preferably, the viscosity of the supplement is 95 centipoises or less. This is ideal for administering the supplement orally because a patient may easily consume a serving having a low viscosity such as that displayed by the present invention. This is also ideal for servings that are tube fed.

The supplement of the present invention is ideal for individuals requiring nutritional support. A variety of regimens can be used. For example, patients can receive servings in the range of 25 to about 100 ml. For example, a patient receiving 60 ml servings would be given 3 to 4 servings per day to provide complete nutritional support. However, for alternate embodiments, the number of servings may differ depending on the nutritional needs of the patient.

The supplement may be in liquid or powder form. In a preferred embodiment, the product is provided in a ready to use liquid form and does not require reconstitution or mixing prior to use. The supplement can be tube fed or administered orally. For example, the supplement can be provided in a can, on spike, and hang bag.

By way of example and not limitation, Table 1 sets forth the nutritional data for two embodiments of the present invention.

TABLE 1

|  | Example No. 1 60:40 Casein Soy | Example No. 2 60:40 + prebiotic |
| --- | --- | --- |
| cal/ml | 2.25 | 2.25 |
| Protein g/liter | 90 | 90 |
| Protein % of cal | 16 | 16 |
| Protein Blend | Caseinate/Soy | Caseinate/Soy |
| Casein:Soy Ratio | 60:40 | 60:40 |
| Fat g/liter | 122.5 | 130 |
| Fat % of cal | 49 | 52 |
| Fat Blend | Canola, Corn | Canola, Corn |
| Carbohydrate g/liter | 197 | 180 |
| Carbohydrate % of cal | 35 | 32 |
| Prebiotic grams | — | 24 |
| Calcium mg/liter | 1230 | 1230 |

TABLE 1-continued

|  | Example No. 1 60:40 Casein Soy | Example No. 2 60:40 + prebiotic |
|---|---|---|
| Phosphorus mg/liter | 1230 | 1230 |
| Magnesium mg/liter | 433 | 433 |
| Sodium mg/liter | 1200 | 1200 |
| Potassium mg/liter | 1733 | 1733 |
| Chloride mg/liter | 1194 | 1194 |
| Vitamin A IU/liter | 7340 | 7340 |
| Vitamin D IU/liter | 489 | 489 |
| Vitamin E IU/liter | 49 | 49 |
| Vitamin K mcg/liter | 87 | 87 |
| Vitamin C mg/liter | 250 | 250 |
| Thiamine mg/liter | 3.5 | 3.5 |
| Riboflavin mg/liter | 4.15 | 4.15 |
| Niacin mg/liter | 48.7 | 48.7 |
| Vitamin B6 mg/liter | 6.9 | 6.9 |
| Folic Acid mcg/liter | 937 | 937 |
| Pantothenic Acid mg/liter | 24.3 | 24.3 |
| Vitamin B12 mcg/liter | 14.4 | 14.4 |
| Biotin mcg/liter | 693 | 693 |
| Choline mg/liter | 500 | 500 |
| Taurine mg/liter | 158 | 158 |
| Iron mg/liter | 22.5 | 22.5 |
| Copper mg/liter | 2.6 | 2.6 |
| Manganese mg/liter | 4.1 | 4.1 |
| Iodine mcg/liter | 181 | 181 |
| Chromium mcg/liter | 50.2 | 50.2 |
| Molybdenum mcg/liter | 161 | 161 |
| Selenium mcg/liter | 73.5 | 73.5 |
| Zinc mg/liter | 60 | 60 |

By way of further example, examples of the product of the present invention are as follows:

EXAMPLE 3

| Ingredient | % |
|---|---|
| Water | 59.9328 |
| Frodex 24 D | 3.2000 |
| Corn Oil/Canola Oil Blend | 10.8200 |
| Acid Casein | 5.7750 |
| Sugar | 4.0000 |
| Soy Protein Isolate | 3.9550 |
| Lecithin | .6000 |
| Vanilla Flavor | .2600 |
| Calcium Citrate*4(H2O) | .2182 |
| VIT Premix | .1700 |
| Potassium Citrate*1(H2O) | .1373 |
| Calcium Hydroxide | .1120 |
| Magnesium Chloride*6(H2O) | .1100 |
| Creamy Mouthfeel Flavor | .1000 |
| Sodium Phosphate Dibasic Anhydrous | .0955 |
| Potassium Hydroxide | .0850 |
| Potassium Phosphate Dibasic Anhydrous | .0815 |
| TR Element Premix | .0700 |
| Sodium Chloride | .0611 |
| Sodium Citrate*2(H2O) | .0511 |
| Citric Acid | .0500 |
| Magnesium Oxide | .0440 |
| Choline Chloride | .0390 |
| Zinc Sulfate*7(H2O) | .0170 |
| Carrageenan | .0105 |
| Antifoam | .0042 |
| Vitamin A | .0008 |
| Total: | 100.0000 |

EXAMPLE NO. 4

| Ingredient | % |
|---|---|
| Water | 59.8739 |
| Corn Oil/Canola Oil Blend | 11.5200 |
| Frodex 24 D | 11.0000 |
| Acid Casein | 5.8000 |
| Sugar | 4.0000 |
| Soy Protein Isolate | 3.9550 |
| Raftilose P95 | 1.7710 |
| Raftiline GR | .7600 |
| Lecithin | .6000 |
| Vanilla Flavor | .2600 |
| Calcium Citrate*4(H2O) | .2184 |
| VIT Premix | .1650 |
| Potassium Citrate*1(H2O) | .1417 |
| Calcium Hydroxide | .1120 |
| Magnesium Chloride*6(H2O) | .1100 |
| Creamy Mouthfeel Flavor | .1000 |
| Sodium Phosphate Dibasic Anhydrous | .0943 |
| Potassium Hydroxide | .0820 |
| Potassium Phosphate Dibasic Anhydrous | .0819 |
| TR Element Premix | .0700 |
| Sodium Chloride | .0634 |
| Sodium Citrate*2(H2O) | .0559 |
| Citric Acid | .0500 |
| Magnesium Oxide | .0440 |
| Choline Chloride | .0390 |
| Zinc Sulfate*7(H2O) | .0170 |
| Carrageenan | .0105 |
| Antifoam | .0042 |
| Vitamin A | .0008 |
| Total: | 100.0000 |

By way of example and not limitation, an example of a process for making the present invention is as follows.

The product can be created by first hydrating the soy protein isolate in water. The acid casein can then be added to the soy protein slurry. The mixture is then allowed to hydrate. The protein slurry is neutralized by a calcium hydroxide/potassium hydroxide solution to a pH of 6.5–6.8. The resulting solution is then subjected to a heat treatment of 266° F. for 5 minutes, followed by flash cooling.

The fat source which may consist of MCTs, corn oil or canola oil singly, or in any combination thereof, is then added into the protein slurry and the mixture is homogenized and cooled. A solution of the carbohydrates, which can be corn syrup solids and sucrose, in addition to carrageenan and monovalent salts is then prepared. The carbohydrate solution is added as well as divalent salts, vitamins, minerals and flavors. The pH of the final mix is adjusted to 6.8–7.1 and the product is thermally processed.

It should be understood that various changes and modifications to the presently preferred embodiments described herein will be apparent to those skilled in the art. Such changes and modifications can be made without departing from the spirit and scope of the invention and without diminishing its attendant advantages. It is therefore intended that such changes and modifications be covered by the appended claims.

What is claimed is:

1. A liquid nutritional product comprising:
   a protein source that provides at least 15% of the total caloric content of the product, the protein source including caseinate and hydrolyzed soy; and
   the product having a caloric density of at least 2.25 calories per ml and a viscosity of 100 centipoises or less.

2. The nutritional product of claim 1 wherein the protein source includes soy protein isolate.

3. The nutritional product of claim 1 including a prebiotic.

4. The nutritional product of claim 1 wherein the protein source comprises at least 90 grams per liter of product.

5. The nutritional product of claim 1 including a fat source comprising at least 50% of the caloric content.

6. A liquid nutritional product comprising:
   a protein source that provides at least 16% of the total caloric content of the product and includes caseinate and hydrolyzed soy protein isolate;
   a fat source comprising at least 40% of the caloric content;
   a carbohydrate source comprising at least 25% of the caloric content; and
   the product has a caloric content of at least 22.5 calories per ml and a viscosity to 100 centipoises or less.

7. The liquid nutritional product of claim 6 wherein the caseinate and soy protein isolate is present at a ratio of approximately 75:25 to about 50:50.

8. The liquid nutritional product of claim 6 including a prebiotic.

9. The liquid nutritional product of claim 6 including a fat source comprising at least 40% of the caloric content.

10. The liquid nutritional product of claim 6 including a carbohydrate source comprising at least 25% of the caloric content.

11. A liquid nutritional product comprising:
    a protein source that provides at least 16% of the total caloric content of the product and includes caseinate;
    a fat source comprising at least 40% of the caloric content;
    a carbohydrate source comprising at least 25% of the caloric content; and
    the product has a caloric content of at least 2.25 calories per ml.

12. The liquid nutritional product of claim 11 wherein the product has a viscosity of 100 centipoises or less.

13. The liquid nutritional product of claim 11 wherein the product provides 90 grams of protein per liter or less.

* * * * *

UNITED STATES PATENT AND TRADEMARK OFFICE
CERTIFICATE OF CORRECTION

PATENT NO. : 6,605,310 B2
DATED : August 12, 2003
INVENTOR(S) : Eileen Fuchs, Chandrasekhara R. Mallangi and Peter Carhuff It is certified that error appears in the above-identified patent and that said Letters Patent is hereby corrected as shown below:

Column 7,
Line 26, please amend the text to read as follows:
-- the product has caloric content of at least 2.25 calories per ml and a viscosity of 100 centipoises or less. --

Signed and Sealed this

Sixth Day of April, 2004

JON W. DUDAS
*Acting Director of the United States Patent and Trademark Office*